United States Patent
Linnestad et al.

(10) Patent No.: US 6,903,205 B2
(45) Date of Patent: Jun. 7, 2005

(54) SEED-PREFERRED PROMOTERS FROM END GENES

(75) Inventors: Casper Linnestad, Vestby (NO);
Kathryn K. Lappegard, West Des Moines, IA (US); Shane E. Abbitt, Ankeny, IA (US); Susan J. Martino-Catt, Grimes, IA (US); Odd-Arne Olsen, Johnston, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 174 days.

(21) Appl. No.: 10/310,191

(22) Filed: Dec. 4, 2002

(65) Prior Publication Data

US 2003/0097689 A1 May 22, 2003

Related U.S. Application Data

(62) Division of application No. 09/383,543, filed on Aug. 26, 1999, now Pat. No. 6,528,704.
(60) Provisional application No. 60/098,230, filed on Aug. 28, 1998.

(51) Int. Cl.[7] .......................... A01H 1/00; C07H 21/04; C12N 5/14; C12N 15/09; C12P 19/34
(52) U.S. Cl. .................. 536/24.1; 435/69.1; 435/91.4; 435/468; 435/419; 435/320.1; 536/23.1; 800/278; 800/295
(58) Field of Search ................ 435/69.1, 91.4, 435/468, 419, 320.1; 536/23.1, 24.1; 800/278, 295

(56) References Cited

PUBLICATIONS

Lalgudi et al. N_Geneseq Database, Accession No. ABX85828, U.S. Pat No. 6,476,212, Nov. 5, 2002, SEQ ID NO:4288.*

Teasdale, RD. N_Geneseq Database, Accession No. AAV18013, WO9813503, Apr. 2, 1998.*

* cited by examiner

*Primary Examiner*—Phuong T. Bui
(74) *Attorney, Agent, or Firm*—Pioneer Hi-Bred International, Inc.

(57) ABSTRACT

The invention provides compositions and methods for regulating expression of heterologous nucleotide sequences in a plant. Compositions are novel nucleotide sequences for seed-preferred promoters isolated from genes for end1 and end2. A method for expressing a heterologous nucleotide sequence in a plant using the disclosed promoter sequences is provided. The method comprises transforming a plant cell to comprise a heterologous nucleotide sequence operably linked to one of the promoters of the invention and regenerating a stably transformed plant from the transformed plant cell.

9 Claims, No Drawings

SEED-PREFERRED PROMOTERS FROM END GENES

CROSS-REFERENCE TO RELATED APPLICATIONS

This application is a divisional of application U.S. Ser. No. 09/383,543 filed Aug. 26, 1999, now issued as U.S. Pat. No. 6,528,704 on Mar. 4, 2003, which application claims the benefit of U.S. application Ser. No. 60/098,230 filed Aug. 28, 1998, now abandoned, which is herein incorporated by reference.

FIELD OF THE INVENTION

The present invention relates to the field of plant molecular biology, more particularly to regulation of gene expression in plants.

BACKGROUND OF THE INVENTION

Expression of heterologous DNA sequences in a plant host is dependent upon the presence of an operably linked promoter that is functional within the plant host. Choice of the promoter sequence will determine when and where within the organism the heterologous DNA sequence is expressed. Where continuous expression is desired throughout the cells of a plant, constitutive promoters are utilized. In contrast, where gene expression in response to a stimulus is desired, inducible promoters are the regulatory element of choice. Where expression in specific tissues or organs are desired, tissue-specific promoters may be used. That is, they may drive expression in specific tissues or organs. Such tissue-specific promoters may be constitutive or inducible. In either case, additional regulatory sequences upstream and/or downstream from the core promoter sequence may be included in expression constructs of transformation vectors to bring about varying levels of expression of heterologous nucleotide sequences in a transgenic plant.

Frequently it is desirable to have constitutive or inducible expression of a DNA sequence in particular tissues or organs of a plant. For example, increased nutritional value of a plant might be accomplished by genetic manipulation of the plant's genome to comprise a seed-preferred promoter operably linked to a heterologous gene such that proteins with enhanced amino acid content are produced in the seed of the plant.

Alternatively, it might be desirable to inhibit expression of a native DNA sequence within a plant's tissues to achieve a desired phenotype. In this case, such inhibition might be accomplished with transformation of the plant to comprise a tissue-specific promoter operably linked to an antisense nucleotide sequence, such that constitutive expression of the antisense sequence produces an RNA transcript that interferes with translation of the mRNA of the native DNA sequence.

Seed development involves embryogenesis and maturation events as well as physiological adaptation processes that occur within the seed to insure progeny survival. Developing plant seeds accumulate and store carbohydrate, lipid, and protein that are subsequently used during germination. Expression of storage protein genes in seeds occurs primarily in the embryonic axis and cotyledons and in the endosperm of developing seeds but rarely in mature vegetative tissues. Generally, the expression patterns of seed proteins are highly regulated. This regulation includes spatial and temporal regulation during seed development. A variety of proteins accumulate and decay during embryogenesis and seed development and provide an excellent system for investigating different aspects of gene regulation as well as for providing regulatory sequences for use in genetic manipulation of plants.

Thus, isolation and characterization of seed-preferred promoters that can serve as regulatory regions for expression of heterologous nucleotide sequences of interest in a seed-preferred manner are needed for genetic manipulation of plants.

SUMMARY OF THE INVENTION

It is an object of the present invention to provide a novel nucleotide sequence for modulating gene expression in a plant.

It is a further object of the present invention to provide an isolated promoter capable of driving transcription in a seed-preferred manner.

It is a further object of the present invention to provide a method of improved control of an endogenous or exogenous product in the seed of a transformed plant.

It is a further object of the present invention to provide a method for providing useful changes in the phenotype of a seed of a transformed plant.

It is a further object of the present invention to provide a method for producing a novel product in the seed of a transformed plant.

It is a further object of the present invention to provide a method for producing a novel function in the seed of a transformed plant.

Therefore, in one aspect, the present invention relates to an isolated nucleic acid comprising an isolated promoter that is capable of driving transcription in a seed-preferred manner, wherein the promoter comprises a nucleotide sequence selected from the group consisting of:

a) a sequence comprising a fragment of the nucleotide sequence set forth in SEQ ID NO: 4; and b) the nucleotide sequence set forth in SEQ ID NO: 4.

In other aspects, the present invention relates to expression cassettes comprising the promoter operably linked to a nucleotide sequence, vectors containing the expression cassette, and plants stably transformed with at least one expression cassette.

In a further aspect, the present invention relates to a method for modulating expression in the seed of a stably transformed plant comprising the steps of (a) transforming a plant cell with an expression cassette comprising the promoter of the present invention operably linked to at least one nucleotide sequence; (b) growing the plant cell under plant growing conditions and (c) regenerating a stably transformed plant from the plant cell wherein expression of the nucleotide sequence alters the phenotype of the seed.

Compositions and methods for regulating expression of heterologous nucleotide sequences in a plant are provided. Compositions are novel nucleotide sequences for seed-preferred plant promoters, more particularly transcriptional initiation regions isolated from the plant genes end1 and end2. A method for expressing a heterologous nucleotide sequence in a plant using the transcriptional initiation sequences disclosed herein is provided. The method comprises transforming a plant cell with a transformation vector that comprises a heterologous nucleotide sequence operably linked to one of the plant promoters of the present invention and regenerating a stably transformed plant from the transformed plant cell. In this manner, the promoter sequences are useful for controlling the expression of endogenous as well as exogenous products in a seed-preferred manner.

Downstream from and under the transcriptional initiation regulation of the seed-specific region will be a sequence of interest which will provide for modification of the phenotype of the seed. Such modification includes modulating the production of an endogenous product, as to amount, relative distribution, or the like, or production of an exogenous expression product to provide for a novel function or product in the seed.

DETAILED DESCRIPTION OF THE INVENTION

In accordance with the invention nucleotide constructs are provided that allow initiation of transcription in seed. Constructs of the invention comprise regulated transcriptional initiation regions associated with seed formation and seed tissues. Thus, the compositions of the present invention comprise novel nucleotide sequences for plant promoters, particularly seed-preferred promoters, more particularly endosperm specific promoters, for the genes end1 and end2. The end1 promoter drives expression in transfer cells at an early stage in precursor cells and continues expression into mature cells. The end2 promoter drives expression in aleurone cells.

The promoters for these genes may be isolated from the 5' untranslated region flanking their respective transcription initiation sites. Methods for isolation of promoter regions are well known in the art.

The term "isolated" refers to material, such as a nucleic acid, which is: (1) substantially or essentially free from components which normally accompany or interact with it as found in its naturally occurring environment; the isolated material optionally comprises material not found with the material in its natural environment; or (2) if the material is in its natural environment, the material has been synthetically (non-naturally) altered or produced by deliberate human intervention to a composition and/or placed at a locus in the cell (e.g., genome or subcellular organelle) not native to a material found in that environment. The alteration to yield the synthetic material can be performed on the material within or removed from its natural state.

Methods are readily available in the art for the hybridization of nucleic acid sequences. Promoter sequences from other plants may be isolated according to well-known techniques based on their sequence homology to the promoter sequences set forth herein. In these techniques, all or part of the known promoter sequence is used as a probe which selectively hybridizes to other sequences present in a population of cloned genomic DNA fragments (i.e. genomic libraries) from a chosen organism.

For example, the entire promoter sequence or portions thereof may be used as probes capable of specifically hybridizing to corresponding promoter sequences. To achieve specific hybridization under a variety of conditions, such probes include sequences that are unique and are preferably at least about 10 nucleotides in length, and most preferably at least about 20 nucleotides in length. Such probes may be used to amplify corresponding promoter sequences from a chosen organism by the well-known process of polymerase chain reaction (PCR). This technique may be used to isolate additional promoter sequences from a desired organism or as a diagnostic assay to determine the presence of the promoter sequence in an organism.

Such techniques include hybridization screening of plated DNA libraries (either plaques or colonies; see e.g. Innis et al. (1990) *PCR Protocols, A Guide to Methods and Applications*, eds., Academic Press).

The terms "stringent conditions" or "stringent hybridization conditions" includes reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

For purposes of defining the invention preferably low stringency conditions are employed including hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. More preferably moderate stringency conditions are employed including hybridization in 40 to 45% formamide, 1 M NaCl, 1% SDS at 37° C., and a wash in 0.5× to 1×SSC at 55 to 60° C. Most preferably high stringency conditions are employed including hybridization in 50% formamide, 1 M NaCl, 1% SDS at 37° C., and a wash in 0.1×SSC at 60 to 65° C. Hybridization times are not critical and can range from about four hours to about sixteen hours.

An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y. (1993); and Current Protocols in Molecular Biology, Chapter 2, Ausubel et al., Eds., Greene Publishing and Wiley-Interscience, New York (1995). See Sambrook et al. (1989) Molecular Cloning: A Laboratory Manual (2nd ed. Cold Spring Harbor Laboratory, Cold Spring Harbor, N.Y.) In general, sequences that correspond to promoter sequences of the invention and hybridize to the promoter sequence disclosed herein will be at least 50% homologous, preferably 60%, 70%, 80%, 85%, 90%, and even 95% homologous or more with the disclosed sequences.

The promoter regions of the invention may be isolated from any plant, including, but not limited to corn (*Zea mays*), (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), oats, barley, vegetables, ornamentals, and conifers. Preferably plants include corn, soybean, sunflower, safflower, oil seed *Brassica*, wheat, rice, barley, rye, alfalfa, and *sorghum*.

The coding sequence expressed by the promoters of the invention may be used for varying the phenotype of the seeds. Various changes in phenotype are of interest including modifying the fatty acid composition in seeds, altering the starch or carbohydrate profile, altering the amino acid content of the seed, and the like. These results can be achieved by providing expression of heterologous or increased expression of endogenous products in seeds. Alternatively, the results can be achieved by providing for a reduction of expression of one or more endogenous products, particularly enzymes or cofactors in the seed. These changes result in a change in phenotype of the transformed seed.

Genes of interest include, generally, those involved in oil, starch, protein, carbohydrate or nutrient metabolism as well as those affecting kernel size, sucrose loading, and the like. In particular, end1 may find use in regulating the influx of nutrients. Both promoters are useful in disease resistance and in regulating expression of phytate genes particularly to lower phytate levels in the seed.

General categories of genes of interest for the purpose of present invention include for example, those genes involved in information, such as Zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, and grain characteristics. It is recognized that any gene of interest can be operably linked to the promoter of the invention and expressed in the seed.

Important traits such as oil, starch and protein content can be genetically altered in addition to using traditional breeding methods. Modifications include altering the content of oleic acid, saturated and unsaturated oils, increasing levels of lysine and sulfur-containing amino acids and providing other essential amino acids, and also modification of starch. Hordothionin protein modifications are described in WO94/16078; WO96/38562; WO96/08220; and U.S. Pat. No. 5,703,409 issued Dec. 30, 1997, the disclosures of which are incorporated herein in their entirety by reference. Another example is lysine and/or sulfur rich seed protein encoded by the soybean 2S albumin described in WO97/35023, and the chymotrypsin inhibitor from barley, Williamson et al. (1987) *Eur. J. Biochem.* 165:99–106, the disclosures of each are incorporated by reference. Derivatives of the following genes can be made by site directed mutagenesis to increase the level of preselected amino acids in the encoded polypeptide. For example, the gene encoding the barley high lysine polypeptide (BHL), is derived from barley chymotrypsin inhibitor, WO98/20133, incorporated herein by reference. Other proteins include methionine-rich plant proteins such as from sunflower seed (Lilley et al. (1989) *Proceedings of the World Congress on Vegetable Protein Utilization in Human Foods and Animal Feedstuffs*; Applewhite, H. (ed.); American Oil Chemists Soc., Champaign, Ill., 497–502, incorporated herein in its entirety by reference), corn (Pedersen et al. (1986) *J. Biol. Chem.* 261:6279; Kirihara et al. (1988) *Gene* 71:359, both incorporated herein in its entirety by reference) and rice (Musumura et al. (1989) *Plant Mol. Biol.* 12:123, incorporated herein in its entirety by reference). Other agronomically important genes encode latex, Floury 2, growth factors, seed storage factors and transcription factors.

The quality of grain is reflected in traits such as levels and types of oils, saturated and unsaturated, quality and quantity of essential amino acids, and levels of cellulose. In corn, modified hordothionin proteins, described in WO94/16078; WO96/38562; WO96/08220; and U.S. Pat. No. 5,703,409; provide descriptions of modifications of proteins for desired purposes.

Commercial traits can also be encoded on a gene(s) which could alter or increase for example, starch for the production of paper, textiles, and ethanol, or provide expression of proteins with other commercial uses. Another important commercial use of transformed plants is the production of polymers and bioplastics such as described in U.S. Pat. No. 5,602,321 issued Feb. 11, 1997. Genes such as B-ketothiolase, PHBase (polyhydroxyburyrate synthase) and acetoacetyl-CoA reductase (see Schubert et al. (1988) *J. Bacteriol* 170(12):5837–5847) facilitate expression of polyhyroxyalkanoates (PHAs).

Exogenous products include plant enzymes and products as well as those from other sources including prokaryotes and other eukaryotes. Such products include enzymes, cofactors, hormones, and the like. The level of seed proteins, particularly modified seed proteins having improved amino acid distribution to improve the nutrient value of the seed can be increased. This is achieved by the expression of such proteins having enhanced amino acid content.

Insect resistance genes may encode resistance to pests that have great yield drag such as rootworm, cutworm, European Corn Borer, and the like. Such genes include, for example, *Bacillus thuringiensis* endotoxin genes (U.S. Pat. Nos. 5,366,892; 5,747,450; 5,737,514; 5,723,756; 5,593,881; Geiser et al. (1986) *Gene* 48:109); lectins (Van Damme et al. (1994) *Plant Mol. Biol.* 24:825); and the like.

Genes encoding disease resistance traits may include detoxification genes, such as against fumonosin (U.S. patent application Ser. No. 08/484,815 filed Jun. 7, 1995); avirulence (avr) and disease resistance (R) genes (Jones et al. (1994) *Science* 266:789; Martin et al. (1993) *Science* 262:1432; Mindrinos et al. (1994) *Cell* 78:1089; and the like.

Agronomic traits in seeds can be improved by altering expression of genes that affect the response of seed growth and development during environmental stress, Cheikh-N et al (1994) *Plant Physiol.* 106(1):45–51) and genes controlling carbohydrate metabolism to reduce kernel abortion in maize, Zinselmeier et al. (1995) *Plant Physiol.* 107(2):385–391.

As noted, the heterologous nucleotide sequence operably linked to one of the promoters disclosed herein may be an antisense sequence for a targeted gene. By "antisense DNA nucleotide sequence" is intended a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing to the endogenous messenger RNA (mRNA) produced by transcription of the DNA nucleotide sequence for the targeted gene. In this case, production of the native protein encoded by the targeted gene is inhibited to achieve a desired phenotypic response. Thus the promoter sequences disclosed herein may be operably linked to antisense DNA sequences to reduce or inhibit expression of a native protein in the plant seed.

By "promoter" or "transcriptional initiation region" is intended a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate. It is recognized that having identified the nucleotide sequences for the promoter regions disclosed herein, it is within the state of the art to isolate and identify further regulatory elements in the 5' untranslated region upstream from the particular promoter regions identified herein. Thus the promoter regions disclosed herein are generally further defined by comprising upstream regulatory elements such as those responsible for tissue and temporal expression of the coding sequence, enhancers and the like. In the same manner, the promoter elements which enable expression in the desired tissue such as the seed can be identified, isolated, and used with other core promoters to confirm seed-preferred expression.

The regulatory sequences of the present invention, when operably linked to a heterologous nucleotide sequence of interest and inserted into a transformation vector, enable seed-preferred expression of the heterologous nucleotide sequence in the seeds of a plant stably transformed with this vector.

By "seed-preferred" is intended expression in the seed, including at least one of embryo, kernel, pericarp, endosperm, nucellus, aleurone, pedicel, and the like.

By "heterologous nucleotide sequence" is intended a sequence that is not naturally occurring with the promoter sequence. While this nucleotide sequence is heterologous to the promoter sequence, it may be homologous, or native, or heterologous, or foreign, to the plant host.

It is recognized that the promoters may be used with their native coding sequences to increase or decrease expression resulting in a change in phenotype in the transformed seed.

The isolated promoter sequences of the present invention can be modified to provide for a range of expression levels of the heterologous nucleotide sequence. Thus, less than the entire promoter regions may be utilized and the ability to drive seed-preferred expression retained. However, it is recognized that expression levels of mRNA may be decreased with deletions of portions of the promoter sequences. Generally, at least about 20 nucleotides of an isolated promoter sequence will be used to drive expression of a nucleotide sequence.

It is recognized that to increase transcription levels enhancers may be utilized in combination with the promoter regions of the invention. Enhancers are nucleotide sequences that act to increase the expression of a promoter region. Enhancers are known in the art and include the SV40 enhancer region, the 35S enhancer element, and the like.

Modifications of the isolated promoter sequences of the present invention can provide for a range of expression of the heterologous nucleotide sequence. Thus, they may be modified to be weak promoters or strong promoters. Generally, by "weak promoter" is intended a promoter that drives expression of a coding sequence at a low level. By "low level" is intended at levels of about 1/10,000 transcripts to about 1/100,000 transcripts to about 1/500,000 transcripts. Conversely, a strong promoter drives expression of a coding sequence at a high level, or at about 1/10 transcripts to about 1/00 transcripts to about 1/1,000 transcripts.

The nucleotide sequences for the promoters of the present invention may be the naturally occurring sequences or sequences having substantial homology. By "substantial homology" is intended a sequence exhibiting substantial functional and structural equivalence with the naturally occurring sequence. Any structural differences between substantially homologous sequences do not effect the ability of the sequence to function as a promoter as disclosed in the present invention. Thus, sequences having substantial sequence homology with the sequence of a particular seed-preferred promoter of the present invention will direct seed-preferred expression of an operably linked heterologous nucleotide sequence. Two promoter nucleotide sequences are considered substantially homologous when they have at least about 70%, preferably at least about 80%, more preferably at least about 90%, still more preferably at least about 95% sequence homology. Substantially homologous sequences of the present invention include variants of the disclosed sequences such as those that result from site-directed mutagenesis, as well as synthetically derived sequences.

Substantially homologous sequences of the present invention also refer to those fragments of a particular promoter nucleotide sequences disclosed herein that operate to promote the seed-preferred expression of an operably linked heterologous nucleotide sequence. These fragments will comprise at least about 20 contiguous nucleotides, preferably at least about 50 contiguous nucleotides, more preferably at least about 75 contiguous nucleotides, even more preferably at least about 100 contiguous nucleotides of the particular promoter nucleotide sequence disclosed herein. The nucleotides of such fragments will usually comprise the TATA recognition sequence of the particular promoter sequence. Such fragments may be obtained by use of restriction enzymes to cleave the naturally occurring promoter nucleotide sequences disclosed herein; by synthesizing a nucleotide sequence from the naturally occurring promoter DNA sequence; or may be obtained through the use of PCR technology. See particularly, Mullis et al. (1987) *Methods Enzymol.* 155:335–350, and Erlich, ed. (1989) *PCR Technology* (Stockton Press, N.Y.). Again, variants of these promoter fragments, such as those resulting from site-directed mutagenesis, are encompassed by the compositions of the present invention.

Nucleotide sequences comprising at least about 40 contiguous sequences of the sequences set forth in SEQ ID NOS: 1 and 4 are encompassed. These sequences may be isolated by hybridization, PCR, and the like. Such sequences encompass fragments capable of driving seed-preferred expression, fragments useful as probes to identify similar sequences, as well as elements responsible for temporal or tissue specificity. Biologically active variants of the promoter sequences are also encompassed by the method of the present invention. Such variants should retain promoter activity, particularly the ability to drive expression in seed or seed tissues. Biologically active variants include, for example, the native promoter sequences of the invention having one or more nucleotide substitutions, deletions or insertions. Promoter activity may be measured by Northern blot analysis, reporter activity measurements when using transcriptional fusions, and the like. See, for example, Sambrook et al. (1989) *Molecular Cloning: A Laboratory Manual* (2nd ed. Cold Spring Harbor Laboratory, Cold Spring Harbor, N.Y.), herein incorporated by reference.

The following terms are used to describe the sequence relationships between two or more nucleic acids or polynucleotides: (a) "reference sequence", (b) "comparison window", (c) "percentage of sequence identity", and (d) "substantial identity".

(a) As used herein, "reference sequence" is a defined sequence used as a basis for sequence comparison. A reference sequence may be a subset or the entirety of a specified sequence; for example, as a segment of a full-length promoter sequence, or the complete promoter sequence.

(b) As used herein, "comparison window" makes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length and optionally can be 30, 40, 50, 100, or more contiguous nucleotides in length. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Optimal alignment of sequences for comparison may be conducted by the homology alignment algorithm of Needleman and Wunsch (1970) *J. Mol. Biol.* 48:443; by computerized implementations of these algorithms, including, but not limited to: GAP, BESTFIT, BLAST, FASTA, and TFASTA in the Wisconsin Genetics Software Package, Genetics Computer Group (GCG) (575 Science Drive, Madison, Wis.). An example of the BLAST family of programs, which can be used to search database sequence similarity for the purposes of this invention, includes BLASTN program for nucleotide query sequences against nucleotide sequence dataset. See, Ausubel et al., eds. (1995) *Current Protocols in Molecular Biology*, Chapter 19 (Greene Publishing and Wiley-Interscience, New York).

The BLAST homology alignment algorithm is useful for comparing fragments of the reference nucleotide or amino acid sequence to sequences from public databases. It is then necessary to apply a method of aligning the complete reference sequence against the complete public sequence to establish a % identity (in the case of polynucleotides) or % similarity (in the case of polypeptides). The GAP algorithm is such a method.

GAP uses the algorithm of Needleman and Wunsch (*J. Mol. Biol.* 48:443–453, 1970) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater. Unless otherwise stated, for purposes of the invention, the preferred method of determining percent sequence identity is by the GAP version 10 algorithm using default parameters.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff & Henikoff (1989) *Proc. Natl. Acad. Sci. USA* 89:10915).

(c) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison and multiplying the result by 100 to yield the percentage of sequence identity.

(d) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters.

Another indication that nucleotide sequences are substantially identical is if two nucleic acid molecules hybridize to each other under stringent conditions. Generally, stringent temperature conditions are selected to be about 5° C. to about 2° C. lower than the melting point ($T_m$) for the specific sequence at a defined ionic strength and pH. The denaturation or melting of DNA occurs over a narrow temperature range and represents the disruption of the double helix into its complementary single strands. The process usually is characterized by the temperature of the midpoint of transition, $T_m$, which is sometimes described as the melting temperature. Formulas are available in the art for the determination of melting temperatures. Typically, stringent wash conditions are those in which the salt concentration is about 0.02 molar at pH 7 and the temperature is at 50, 55, or 60° C.

The nucleotide sequences for the seed-preferred promoters disclosed in the present invention, as well as variants and fragments thereof, are useful in the genetic manipulation of any plant when operably linked with a heterologous nucleotide sequence whose expression is to be controlled to achieve a desired phenotypic response. By "operably linked" is intended the transcription or translation of the heterologous nucleotide sequence is under the influence of the promoter sequence. In this manner, the nucleotide sequences for the promoters of the invention may be provided in expression cassettes along with heterologous nucleotide sequences for expression in the plant of interest, more particularly in the seed of the plant.

Such expression cassettes will comprise a transcriptional initiation region comprising one of the promoter nucleotide sequences of the present invention, or variants or fragments thereof, operably linked to the heterologous nucleotide sequence whose expression is to be controlled by the seed-preferred promoters disclosed herein. Such an expression cassette is provided with a plurality of restriction sites for insertion of the nucleotide sequence to be under the transcriptional regulation of the regulatory regions. The expression cassette may additionally contain selectable marker genes.

The expression cassette will include in the 5'-to-3' direction of transcription, a transcriptional and translational initiation region, a heterologous nucleotide sequence of interest, and a transcriptional and translational termination region functional in plants. The termination region may be native with the transcriptional initiation region comprising one of the promoter nucleotide sequences of the present invention, may be native with the DNA sequence of interest, or may be derived from another source. Convenient termination regions are available from the Ti-plasmid of *A. tumefaciens*, such as the octopine synthase and nopaline synthase termination regions. See also, Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; Joshi et al. (1987) *Nucleic Acid Res.* 15:9627–9639.

The expression cassette comprising the promoter sequence of the present invention operably linked to a heterologous nucleotide sequence may also contain at least one additional nucleotide sequence for a gene to be cotransformed into the organism. Alternatively, the additional sequence(s) can be provided on another expression cassette.

Where appropriate, the heterologous nucleotide sequence whose expression is to be under the control of the promoter sequence of the present invention and any additional nucleotide sequence(s) may be optimized for increased expression in the transformed plant. That is, these nucleotide sequences can be synthesized using plant preferred codons for improved expression. Methods are available in the art for synthesizing plant-preferred nucleotide sequences. See, for example, U.S. Pat. Nos. 5,380,831 and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the heterologous nucleotide sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Nat. Acad. Sci. USA* 86:6126–6130); potyvirus leaders, for example, TEV leader (Tobacco Etch Virus) (Allison et al. (1986)); MDMV leader (Maize Dwarf Mosaic Virus) (*Virology* 154:9–20); human immunoglobulin heavy-chain binding protein (BiP) (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) *Molecular Biology of RNA*, pages 237–256); and maize chlorotic mottle virus leader (MCMV) (Lommel et al. (1991) *Virology* 81:382–385). See also Della-Cioppa et al. (1987) *Plant Physiology* 84:965–968. Other methods known to enhance translation and/or mRNA stability can also be utilized, for example, introns, and the like.

In those instances where it is desirable to have the expressed product of the heterologous nucleotide sequence directed to a particular organelle, particularly the plastid, amyloplast or vacuole, or to the endoplasmic reticulum, or secreted at the cell's surface or extracellularly, the expression cassette may further comprise a coding sequence for a transit peptide. Such transit peptides are well known in the art and include, but are not limited to, the transit peptide for the acyl carrier protein, the small subunit of RUBISCO, plant EPSP synthase, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, for example, transitions and transversions, may be involved.

Reporter genes or selectable marker genes may be included in the expression cassette. Examples of suitable reporter genes known in the art can be found in, for example, Jefferson et al. (1991) in *Plant Molecular Biology Manual*, ed. Gelvin et al. (Kluwer Academic Publishers), pp. 1–33; DeWet et al. (1987) *Mol. Cell. Biol.* 7:725–737; Goff et al. (1990) *EMBO J.* 9:2517–2522; Kain et al. (1995) *Bio Techniques* 19:650–655; and Chiu et al. (1996) *Current Biology* 6:325–330.

Selectable marker genes for selection of transformed cells or tissues can include genes that confer antibiotic resistance or resistance to herbicides. Examples of suitable selectable marker genes include, but are not limited to, genes encoding resistance to chloramphenicol (Herrera Estrella et al. (1983) *EMBO J.* 2:987–992); methotrexate (Herrera Estrella et al. (1983) *Nature* 303:209–213; Meijer et al. (1991) *Plant Mol. Biol.* 16:807–820); hygromycin (Waldron et al. (1985) *Plant Mol. Biol.* 5:103–108; Zhijian et al. (1995) *Plant Science* 108:219–227); streptomycin (Jones et al. (1987) *Mol. Gen. Genet.* 210:86–91); spectinomycin (Bretagne-Sagnard et al. (1996) *Transgenic Res.* 5:131–137); bleomycin (Hille et al. (1990) *Plant Mol. Biol.* 7:171–176); sulfonamide (Guerineau et al. 1990) *Plant Mol. Biol.* 15:127–136); bromoxynil (Stalker et al. (1988) *Science* 242:419–423); glyphosate (Shaw et al. (1986) *Science* 233:478–481); phosphinothricin (DeBlock et al. (1987) *EMBO J.* 6:2513–2518).

Other genes that could serve utility in the recovery of transgenic events but might not be required in the final product would include, but are not limited to, examples such as GUS (b-glucoronidase; Jefferson (1987) *Plant Mol. Biol. Rep.* 5:387), GFP (green florescence protein; Chalfie et al. (1994) *Science* 263:802), luciferase (Riggs et al. (1987) *Nucleic Acids Res.* 15(19):8115 and Luehrsen et al. (1992)

*Methods Enzymol.* 216:397–414) and the maize genes encoding for anthocyanin production (Ludwig et al. (1990) *Science* 247:449).

The expression cassette comprising the particular promoter sequence of the present invention operably linked to a heterologous nucleotide sequence of interest can be used to transform any plant. In this manner, genetically modified plants, plant cells, plant tissue, seed, and the like can be obtained.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat No. 5,563,055; Zhao et al. WO US98/01268), direct gene transfer (Paszkowski et al. (1984) *EMBO J.* 3:2717–2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature* (London) 311:763–764; Bowen et al., U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, N.Y.), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

The following examples are offered by way of illustration and not by way of limitation.

Experimental

Promoter regions for the maize genes end1 and end2 were isolated from maize plants and cloned. These genes were selected as sources of seed-preferred promoters based on the spatial expression of their gene products. The method for their isolation is described below.

EXAMPLE 1

Isolation of Promoter Sequences

The procedure for promoter isolation is described in the User Manual for the Genome Walker kit sold by Clontech Laboratories, Inc., Palo Alto, Calif. Genomic DNA from maize line A63 was prepared by grinding 10-day-old seedling leaves in liquid nitrogen, and the DNA prepared as described by Chen and Dellaporta (1994) in The Maize Handbook, ed. Freeling and Walbot (Springer-Verlag, Berlin) with a few minor modifications. Precipitated DNA was recovered using an inoculation loop and transferred to a 1.5 ml eppendorf tube containing 500 µl of TE(10 mM Tris pH 8.0, 1 mM EDTA). The DNA was allowed to dissolve at room temperature for 15 minutes, phenol extracted and 2-propanol precipitated in 700 µl. The precipitate was recovered and washed with 70% ethanol. The DNA was then placed in a clean 1.5 ml eppendorf tube to air dry and resuspended in 200 µl of TE. RNase A was added to 10 µg/ml and the mixture was incubated at 37° C. for several hours. The DNA was then extracted once with phenol-chloroform, then chloroform, then ethanol precipitated and resuspended in TE. The DNA was then used exactly as described in the Genome Walker User Manual (Clontech PT3042-1 version PR68687). Briefly, the DNA was digested separately with restriction enzymes DraI, EcoRV, PvuII, ScaI, and StuI, all blunt-end cutters. The DNA was extracted with phenol, then chloroform, then ethanol precipitated. The Genome Walker adapters were ligated onto the ends of the restricted DNA. The resulting DNA is referred to as DL1-DL5, respectively.

For isolation of specific promoter regions, two nonoverlapping gene-specific primers (27–30 bp in length) were designed from the 5' end of the maize genes identified from sequence databases. The primers were designed to amplify the region upstream of the coding sequence, i.e. the 5' untranslated region and promoter of the chosen gene. The sequence of the primers are given below for each promoter described. The first round of PCR was performed on each DNA sample (DL1-5) with Clontech primer AP1 (sequence 5'-gtaatacgactcactatagggc-3') and the gene-specific primer (gsp)1 with the sequences shown in SEQ ID NOS: 2 and 5.

PCR was performed in a model PTC-100 thermal cycler with HotBonnet from MJ Research (Watertown, Mass.) using reagents supplied with the Genome Walker kit. The following cycle parameters were used: 7 cycles of 94° C. for 2 seconds, then 72° C. for 3 minutes, followed by 32 cycles of 94° C. for 2 seconds and 67° C. for 3 minutes. Finally, the samples were held at 67° C. for 4 minutes and then at 4° C. until further analysis.

As described in the User Manual, the DNA from the first round of PCR was then diluted and used as a template in a second round of PCR using the Clontech AP2 primer (sequence 5'-actatagggcacgcgtggt-3') and gene-specific primer (gsp)2 with the sequences shown in SEQ ID NOS: 3 and 6.

The cycle parameters for the second round were: 5 cycles of 94° C. for 2 seconds, then 72° C. for 3 minutes. Finally, the samples were held at 67° C. for 4 minutes and then held at 4° C. Approximately 10 µl of each reaction were run on a 0.8% agarose gel, and bands (usually 500 bp or larger) were excised, purified with the Sephaglas BandPrep kit (Pharmacia, Piscataway, N.J.) and cloned into the TA vector pCR2.1 (Invitrogen, San Diego, Calif.). Clones were sequenced for verification.

EXAMPLE 2

Expression Data Using Promoter Sequences

Three promoter::GUS fusion constructs were prepared by the methods described below. All vectors were constructed using standard molecular biology techniques (Sambrook et al., Supra). A reporter gene and a selectable marker gene for gene expression and selection was inserted between the multiple cloning sites of the pBluescript cloning vector (Stratagene Inc., 11011 N. Torrey Pines Rd., La Jolla, Calif.). The reporter gene was the β-glucuronidase (GUS) gene (Jefferson, R. A. et al., 1986, *Proc. Natl. Acad. Sci.* (USA) 83:8447–8451) into whose coding region was inserted the second intron from the potato ST-LS1 gene (Vancanneyt et al., *Mol. Gen. Genet.* 220:245–250, 1990), to produce intron-GUS, in order to prevent expression of the gene in *Agrobacterium* (see Ohta, S. et al., 1990, *Plant Cell Physiol.* 31(6):805–813). The respective promoter regions were ligated in frame to sites 5' to the GUS gene. A fragment containing bases 2 to 310 from the terminator of the potato proteinase inhibitor (pinII) gene (An et al., *Plant Cell* 1:115–122, 1989) was blunt-end ligated downstream of the GUS coding sequence, to create the GUS expression cassette. The 3' end of the terminator carried a NotI restriction site.

The promoter fusion end1::GUS::pinII was constructed using the GUS::pinII plasmid digested with BamHI, filled in with Klenow, and digested with NcoI. The promoter was isolated from the TOPOTA vector by digestion with AvaI, filled in with Klenow, and then digestion with NcoI. The fragment was ligated into the digested expression cassette, and successful subcloning was confirmed by restriction digest and sequencing.

The *Agrobacterium* transformation plasmids were constructed by inserting the GUS expression cassette as a HindIII/NotI fragment and the BAR expression cassette as a NotI/SacI fragment between the right and left T-DNA borders in pSB11 at HindIII and SacI sites. The GUS cassette was inserted proximal to the right T-DNA border. The plasmid pSB11 was obtained from Japan Tobacco Inc. (Tokyo, Japan). The construction of pSB11 from pSB21 and the construction of pSB21 from starting vectors is described by Komari et al. (1996, *Plant J.* 10:165–174). The T-DNA of the plasmids were integrated into the superbinary plasmid pSB1 (Saito et al., EP 672 752 A1) by homologous recombination between the two plasmids. The plasmid pSB1 was also obtained from Japan Tobacco Inc. *E. coli* strain HB101 containing the expression cassettes was mated with *Agrobacterium* strain LBA4404 harboring pSB1 to create the cointegrate plasmid in *Agrobacterium* using the method of Ditta et al., (*Proc. Natl. Acad. Sci.* USA 77:7347–7351, 1980). Successful recombination was verified by a SalI restriction digest of the plasmid.

EXAMPLE 3

Transformation and Regeneration of Maize Callus via *Agrobacterium*

Preparation of *Agrobacterium* Suspension:

*Agrobacterium* is streaked out from a −80° frozen aliquot onto a plate containing PHI-L medium and cultured at 28° C. in the dark for 3 days. PHI-L media comprises 25 ml/l Stock Solution A, 25 ml/l Stock Solution B, 450.9 ml/l Stock Solution C and spectinomycin (Sigma Chemicals) added to a concentration of 50 mg/l in sterile ddH2O (stock solution A: K2HPO4 60.0 g/l, NaH2PO4 20.0 g/l, adjust pH to 7.0 w/KOH and autoclave; stock solution B: NH4Cl 20.0 g/l, MgSO4.7H2O 6.0 g/l, KCl 3.0 g/l, CaCl2 0.20 g/l, FeSO4.7H2O 50.0 mg/l, autoclave; stock solution C: glucose 5.56 g/l, agar 16.67 g/l (#A-7049, Sigma Chemicals, St. Louis, Mo.) and autoclave).

The plate can be stored at 4° C. and used usually for about 1 month. A single colony is picked from the master plate and streaked onto a plate containing PHI-M medium [yeast extract (Difco) 5.0 g/l; peptone (Difco) 10.0 g/l; NaCl 5.0 g/l; agar (Difco) 15.0 g/l; pH 6.8, containing 50 mg/L spectinomycin] and incubated at 28° C. in the dark for 2 days.

Five ml of either PHI-A, [CHU(N6) basal salts (Sigma C-1416) 4.0 g/l, Eriksson's vitamin mix (1000X, Sigma-1511) 1.0 ml/l; thiamine.HCl 0.5 mg/l (Sigma); 2,4-dichlorophenoxyacetic acid (2,4-D, Sigma) 1.5 mg/l; L-proline (Sigma) 0.69 g/l; sucrose (Mallinckrodt) 68.5 g/l; glucose (Mallinckrodt) 36.0 g/l; pH 5.2] for the PHI basic medium system, or PHI-I [MS salts (GIBCO BRL) 4.3 g/l; nicotinic acid (Sigma) 0.5 mg/l; pyridoxine.HCl (Sigma) 0.5 mg/l; thiamine.HCl 1.0 mg/l; myo-inositol (Sigma) 0.10 g/l; vitamin assay casamino acids (Difco Lab) 1.0 g/l; 2, 4-D 1.5 mg/l; sucrose 68.50 g/l; glucose 36.0 g/l; adjust pH to 5.2 w/KOH and filter-sterilize] for the PHI combined medium system and 5 ml of 100 mM (3'-5'-Dimethoxy-4'-hydroxyacetophenone, Aldrich chemicals) are added to a 14 ml Falcon tube in a hood. About 3 full loops (5 mm loop size) *Agrobacterium* is collected from the plate and suspended in the tube, then the tube is vortexed to make an even suspension. One ml of the suspension is transferred to a spectrophotometer tube and the OD of the suspension adjusted to 0.72 at 550 nm by adding either more *Agrobacterium* or more of the same suspension medium, for an *Agrobacterium* concentration of approximately 0.5×109 cfu/ml to 1×109 cfu/ml. The final *Agrobacterium* suspension is aliquoted into 2 ml microcentrifuge tubes, each containing 1 ml of the suspension. The suspensions are then used as soon as possible.

Embryo isolation, infection and co-cultivation:

About 2 ml of the same medium (here PHI-A or PHI-I) used for the *Agrobacterium* suspension are added into a 2 ml microcentrifuge tube. Immature embryos are isolated from a sterilized ear with a sterile spatula (Baxter Scientific Products S1565) and dropped directly into the medium in the tube. A total of about 100 embryos are placed in the tube. The optimal size of the embryos is about 1.0–1.2 mm. The cap is then closed on the tube and the tube vortexed with a Vortex Mixer (Baxter Scientific Products S8223-1) for 5 sec. at maximum speed. The medium is removed and 2 ml of fresh medium are added and the vortexing repeated. All of the medium is drawn off and 1 ml of *Agrobacterium* suspension is added to the embryos and the tube vortexed for 30 sec. The tube is allowed to stand for 5 min. in the hood. The suspension of *Agrobacterium* and embryos was poured into a Petri plate containing either PHI-B medium [CHU (N6) basal salts (Sigma C-1416) 4.0 g/l; Eriksson's vitamin mix (100X, Sigma-1511) 1.0 ml/l; thiamine.HCl 0.5 mg/l; 2.4-D 1.5 mg/l; L-proline 0.69 g/l; silver nitrate 0.85 mg/l; gelrite (Sigma) 3.0 g/l; sucrose 30.0 g/l; acetosyringone 100 mM; pH 5.8], for the PHI basic medium system, or PHI-J medium [MS Salts 4.3 g/l; nicotinic acid 0.50 mg/l; pyridoxine HCl 0.50 mg/l; thiamine.HCl 1.0 mg/l; myo-inositol 100.0 mg/l; 2, 4-D 1.5 mg/l; sucrose 20.0 g/l; glucose 10.0 g/l; L-proline 0.70 g/l; MES (Sigma) 0.50 g/l; 8.0 g/l agar (Sigma A-7049, purified) and 100 mM acetosyringone with a final pH of 5.8 for the PHI combined medium system. Any embryos left in the tube are transferred to the plate using a sterile spatula. The *Agrobacterium* suspension is drawn off and the embryos placed axis side down on the media. The plate is sealed with Parafilm tape or Pylon Vegetative Combine Tape (product named "E.G.CUT" and is available in 18 mm×50 m sections; Kyowa Ltd., Japan) and incubated in the dark at 23–25° C. for about 3 days of co-cultivation.

Resting, Selection and Regeneration Steps:

For the resting step, all of the embryos are transferred to a new plate containing PHI-C medium [CHU(N6) basal salts (Sigma C-1416) 4.0 g/l; Eriksson's vitamin mix (1000X Sigma-1511) 1.0 ml/l; thiamine.HCl 0.5 mg/l; 2.4-D 1.5 mg/l; L-proline 0.69 g/l; sucrose 30.0 g/l; MES buffer (Sigma) 0.5 g/l; agar (Sigma A-7049, purified) 8.0 g/l; silver nitrate 0.85 mg/l; carbenicillin 100 mg/l; pH 5.8]. The plate is sealed with Parafilm or Pylon tape and incubated in the dark at 28° C. for 3–5 days.

Longer co-cultivation periods may compensate for the absence of a resting step since the resting step, like the co-cultivation step, provides a period of time for the embryo to be cultured in the absence of a selective agent. Those of ordinary skill in the art can readily test combinations of co-cultivation and resting times to optimize or improve the transformation frequency without undue experimentation.

For selection, all of the embryos are then transferred from the PHI-C medium to new plates containing PHI-D medium, as a selection medium, [CHU(N6) basal salts (SIGMA C-1416) 4.0 g/l; Eriksson's vitamin mix (1000X, Sigma-1511) 1.0 ml/l; thiamine.HCl 0.5 mg/l; 2.4-D 1.5 mg/l; L-proline 0.69 g/l; sucrose 30.0 g/l; MES buffer 0.5 g/l; agar (Sigma A-7049, purified) 8.0 g/l; silver nitrate 0.85 mg/l; carbenicillin (ICN, Costa Mesa, Calif.) 100 mg/l; bialaphos (Meiji Seika K. K., Tokyo, Japan) 1.5 mg/l for the first two weeks followed by 3 mg/l for the remainder of the time.; pH 5.8] putting about 20 embryos onto each plate. The plates are sealed as described above and incubated in the dark at 28° C. for the first two weeks of selection. The embryos are transferred to fresh selection medium at two-week intervals. The tissue is subcultured by transferring to fresh selection medium for a total of about 2 months. The herbicide-resistant calli are then "bulked up" by growing on the same medium for another two weeks until the diameter of the calli is about 1.5–2 cm.

For regeneration, the calli are then cultured on PHI-E medium [MS salts 4.3 g/l; myo-inositol 0.1 g/l; nicotinic acid 0.5 mg/l, thiamine.HCl 0.1 mg/l, Pyridoxine.HCl 0.5 mg/l, Glycine 2.0 mg/l, Zeatin 0.5 mg/l, sucrose 60.0 g/l, Agar (Sigma, A-7049) 8.0 g/l, Indoleacetic acid (IAA, Sigma) 1.0 mg/l, Abscisic acid (ABA, Sigma) 0.1 mM, Bialaphos 3 mg/l, carbenicillin 100 mg/l adjusted to pH 5.6] in, the dark at 28° C. for 1–3 weeks to allow somatic embryos to mature. The calli are then cultured on PHI-F medium (MS salts 4.3 g/l; myo-inositol 0.1 g/l; Thiamine-.HCl 0.1 mg/l, Pyridoxine.HCl 0.5 mg/l, Glycine 2.0 mg/l, nicotinic acid 0.5 mg/l; sucrose 40.0 g/l; gelrite 1.5 g/l; pH 5.6] at 25° C. under a daylight schedule of 16 hrs. light (270 uE m-2 sec-1) and 8 hrs. dark until shoots and roots develop.

Each small plantlet is then transferred to a 25×150 mm tube containing PHI-F medium and grown under the same conditions for approximately another week. The plants are transplanted to pots with soil mixture in a greenhouse. GUS+ events are determined at the callus stage or regenerated plant stage.

For Hi-II a preferred optimized protocol was $0.5 \times 10^9$ cfu/ml *Agrobacterium* a 3–5 day resting step and no AgNO3 in the infection medium (PHI-A medium).

EXAMPLE 4

In Situ Localization of End2 mRNA in Developing Maize Kernel

In situ hybridization was performed using the protocol of Jackson, D. P. (1991) In situ Hybridization in Plants, *Molecular Plant Pathology: A Practical Approach*, D. J. Bowles, S. J. Gurr, and M. McPherson, eds. Oxford University Press, England, pp.63–74. Both a sense and antisense probe corresponding to a protein of the end2 cDNA were used. Probes were labelled non-isotopically with digoxigenin and incubated with various sections of 5 DAP and 9 DAP (days after pollination) kernels of maize line CJ27 which had been fixed and embedded. Following extensive washing to remove unbound probe, sections were incubated with anti-digoxigenin alkaline phosphatase to detect areas of probe hybridization. For end2, mRNA was detected specifically with the antisense probe and restricted to the aleurone layer of endosperm tissue. The sense control probe did not hybridize.

EXAMPLE 5

Northern Analysis of Gene Expression in Vegetative Tissue and Developing Kernels Total RNA (10 µg) was size fractionated on a 1% formaldehyde agarose gel and transformed to a nitrocellular membrane. Membranes were hybridized under stringent conditions with $^{32}$P-labelled probes representing cDNA fragments of the various genes. After extensive washing to remove unbound probe, membranes were exposed on X-ray film. RNA samples were obtained from vegetative tissues as well as)developing maize kernels.

The end1 expression pattern showed no expression in vegetative tissues. End1 was predominantly expressed in early to mid-development whole kernel. Expression was also seen in isolated 7 DAP (days after pollination) embryo, 10 DAP endosperm and 10 DAP pericarp.

The expression pattern of end2 likewise showed no expression in vegetative tissue. End2 showed expression in 9–14 DAP whole kernel. End2 also showed expression in isolated 7 DAP embryo, 10 DAP endosperm, and 10 DAP pericarp.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An isolated promoter that is capable of driving transcription in a seed-preferred manner, wherein the promoter comprises a nucleotide sequence selected from the group consisting of:
   a) a sequence comprising a fragment of the nucleotide sequence set forth in SEQ ID NO: 4; and
   b) the nucleotide sequence set forth in SEQ ID NO: 4.

2. The isolated promoter of claim 1 that is capable of driving transcription in a seed-preferred manner, wherein the promoter comprises a fragment of the nucleotide sequence set forth in SEQ ID NO: 4.

3. The isolated promoter of claim 1 that is capable of driving transcription in a seed-preferred manner, wherein the promoter comprises a nucleotide sequence set forth in SEQ ID NO: 4.

4. An expression cassette comprising a promoter and a nucleotide sequence operably linked to the promoter, wherein the promoter is capable of initiating seed-preferred transcription of the nucleotide sequence in a plant cell, wherein the promoter comprises a nucleotide sequence selected from the group consisting of:
   a) a sequence comprising a fragment of the nucleotide sequence set forth in SEQ ID NO: 4; and
   b) the nucleotide sequence set forth in SEQ ID NO: 4.

5. The expression cassette of claim 4 wherein the promoter comprises a fragment of the nucleotide sequence set forth in SEQ ID NO: 4.

6. The expression cassette of claim 4 wherein the promoter comprises the nucleotide sequence set forth in SEQ ID NO: 4.

7. A plant stably transformed with an expression cassette comprising a maize promoter and a nucleotide sequence operably linked to the promoter, wherein the promoter is capable of initiating seed-preferred transcription of the nucleotide sequence in a plant cell, wherein the promoter comprises a nucleotide sequence selected from the group consisting of:
   a) a sequence comprising a fragment of the nucleotide sequence set forth in SEQ ID NO: 4; and
   b) the nucleotide sequence set forth in SEQ ID NO: 4.

8. The plant of claim 7 wherein the promoter comprises a fragment of the nucleotide sequence set forth in SEQ ID NO: 4.

9. The plant of claim 7 wherein the promoter comprises the nucleotide sequence set forth in SEQ ID NO: 4.

* * * * *

SEQUENCE LISTING

<160> NUMBER OF SEQ ID NOS: 10

<210> SEQ ID NO 1
<211> LENGTH: 713
<212> TYPE: DNA
<213> ORGANISM: Zea mays

<400> SEQUENCE: 1

```
ggctggtaaa aaccattatt aactttaaca tcgaatcaaa actgacaaat tttatacttt      60
cacagagcag cagaaattta tacaatatga ttgaatacaa gatgtaggac ccgatggaga     120
gaattttttt gtctcctata tgcttgaata cccaacataa tatcttcgca gcatactatc     180
tatctaatag aaaaattata atatagttaa atacttaagt agtatctagt ggatagaatt     240
caatatctca tacatgcatg aggagtaata tctactagac atgcaacata tttttatcta     300
tctaatagaa tatatataat aaagttaaat attatatgca tcacctacta tatataattt     360
gatatctttt agatgtataa gggactaaga ataatatctc tagcacacat gcaatgcatt     420
atctatctaa atatattata taatagttaa atattaatta tacgtagtct aaacctacat     480
ataagcctac ccatccccac ttagagatct cagtgtcaca catagaccat acatctcact     540
tcgccaagaa aatttcgtca acagttgaag ttatacccat ggcaaaacta ctcttgggtt     600
tgctccttgc ccttgctatt ctagggacaa catcggctgc tggttgtgta caagaagggc     660
gaattctgca gatatccatc acactggcgg ccgctcgagc atgcatctag agg            713
```

<210> SEQ ID NO 2
<211> LENGTH: 27
<212> TYPE: DNA
<213> ORGANISM: Zea mays

<400> SEQUENCE: 2

```
tgttgggtat tcaagcatat aggagac                                          27
```

<210> SEQ ID NO 3
<211> LENGTH: 29
<212> TYPE: DNA
<213> ORGANISM: Zea mays

<400> SEQUENCE: 3

```
ccatcgggtc ctacatcttg tattcaatc                                        29
```

<210> SEQ ID NO 4
<211> LENGTH: 1224
<212> TYPE: DNA
<213> ORGANISM: Zea mays

<400> SEQUENCE: 4

```
tactataggg cacgcgtggt cgacggcccg ggctggtaaa agtaattga acccaaaata       60
tcatggtatg tttggtgaag acagtgatca gtgatttttt tatatctata tatatatcaa     120
agatacttga ttttctagaa ggttcttttt gttgttttcc cttatgtttt tacgcatgat     180
gcaattcttt ttgagaggtt tccgatgcat tgatgttatt gtattatctc ctatatatag     240
gtcgacgtac attatgtatt gcaataacca gttaactgga tccagcttcg cttagttttt     300
agttttggc agaaaaaatg atcaatgttt cacaaaccaa atattttat aacttttgat       360
gaaagaagat caccacggtc atatctaggg gtggtaacaa attgcgatct aaatgttct     420
tcataaaaaa taaggcttct taataaattt tagttcaaaa taaatacgaa taaagtctga    480
```

```
ttctaatctg attcgatcct taaattttat aatgcaaaat ttagagctca ttaccacctc      540
tagtcatatg tctagtctga ggtatatcca aaaagccctt tctctaaatt ccacacccaa      600
ctcagatgtt tgcaaataaa tactccgact ccaaaatgta ggtgaagtgc aactttctcc      660 atttatatc aacatttgtt attttttgtt taacatttca cactcaaaac taattaataa       720
aatacgtggt tgttgaacgt gcgcacatgt ctcccttaca ttatgttttt ttatttatgt      780
attattgttg ttttcctccg aacaacttgt caacatatca tcattggtct ttaatattta     840
tgaatatgga agcctagtta tttacacttg gctacacact agttgtagtt ttgccacttg      900
tctaacatgc aactctagta gttttgccac ttgcctggca cgcgactcta gtattgacac      960
ttgtatagca aataatgcca atacgacacc tggccttaca tgaaacatta tttttgacac     1020
ttgtatacca tgcaacatta ccattgacat ttgtccatac acattatatc aaatatattg    1080
agcgcatgtc acaaactcga tacaaagctg gatgaccctc cctcaccaca tctataaaaa    1140
cccgagcgct actgtaaatc actcacaaca caacacatat cttttagtaa cctttcaata    1200
ggcgtccccc aagaactagt aaac                                            1224
```

<210> SEQ ID NO 5
<211> LENGTH: 30
<212> TYPE: DNA
<213> ORGANISM: Zea mays

<400> SEQUENCE: 5
acttatcagg ctttggaggt cattctcaca                                        30

<210> SEQ ID NO 6
<211> LENGTH: 32
<212> TYPE: DNA
<213> ORGANISM: Zea mays

<400> SEQUENCE: 6
tccatcagca tgagagagcc tatggcaaac at                                     32

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7
gtaatacgac tcactatagg gc                                                22

<210> SEQ ID NO 8
<211> LENGTH: 19
<212> TYPE: DNA
<213> ORGANISM: Artificial Sequence
<220> FEATURE:
<223> OTHER INFORMATION: primer

<400> SEQUENCE: 8
actatagggc acgcgtggt                                                    19

<210> SEQ ID NO 9
<211> LENGTH: 22
<212> TYPE: DNA
<213> ORGANISM: Artificial Sequence
<220> FEATURE:
<223> OTHER INFORMATION: commercial primer AP1

```
<400> SEQUENCE: 9
gtaatacgac tcactatagg gc                                              22

<210> SEQ ID NO 10
<211> LENGTH: 19
<212> TYPE: DNA
<213> ORGANISM: Artificial Sequence
<220> FEATURE:
<223> OTHER INFORMATION: commerical primer AP2

<400> SEQUENCE: 10
actatagggc acgcgtggt                                                  19
```